United States Patent
Itsuki et al.

(10) Patent No.: US 9,131,992 B2
(45) Date of Patent: Sep. 15, 2015

(54) ORTHODONTIC CONNECTION TOOL

(75) Inventors: Yasuhiro Itsuki, Tokyo (JP); Norihisa Okada, Tokyo (JP); Junichi Kono, Ichikawa (JP)

(73) Assignees: Yasuhiro Itsuki, Tokyo (JP); Okada Medical Supply Co., Tokyo (JP)

( * ) Notice: Subject to any disclaimer, the term of this patent is extended or adjusted under 35 U.S.C. 154(b) by 0 days.

(21) Appl. No.: 13/980,031

(22) PCT Filed: Jan. 17, 2012

(86) PCT No.: PCT/JP2012/050810
§ 371 (c)(1),
(2), (4) Date: Sep. 25, 2013

(87) PCT Pub. No.: WO2012/099103
PCT Pub. Date: Jul. 26, 2012

(65) Prior Publication Data
US 2014/0038122 A1   Feb. 6, 2014

(30) Foreign Application Priority Data

Jan. 17, 2011   (JP) .................................. 2011-006980

(51) Int. Cl.
*A61C 7/00* (2006.01)
*A61C 8/00* (2006.01)

(52) U.S. Cl.
CPC *A61C 7/00* (2013.01); *A61C 8/0096* (2013.01)

(58) Field of Classification Search
CPC ...... A61C 7/00; A61C 8/0031; A61C 8/0048; A61C 8/0096; A61C 13/275
USPC .......................... 433/18, 20, 22, 24, 173–174
See application file for complete search history.

(56) References Cited

U.S. PATENT DOCUMENTS

| | | | |
|---|---|---|---|
| 4,516,937 A * | 5/1985 | Bosker | 433/173 |
| 5,427,906 A | 6/1995 | Hansen | |
| 5,567,155 A * | 10/1996 | Hansen | 433/172 |
| 5,853,291 A * | 12/1998 | DeVincenzo et al. | 433/176 |
| 7,559,764 B2 * | 7/2009 | DeVincenzo et al. | 433/18 |
| 7,927,098 B2 * | 4/2011 | Knopfle | 433/18 |
| 8,092,218 B2 * | 1/2012 | Auderset et al. | 433/172 |
| 8,523,567 B2 * | 9/2013 | Allaire | 433/174 |

(Continued)

FOREIGN PATENT DOCUMENTS

| | | |
|---|---|---|
| JP | 11-164843 A | 6/1999 |
| JP | 2003-204973 A | 7/2003 |

(Continued)

OTHER PUBLICATIONS

International Search Report, PCT/JP2012/050810, dated Apr. 17, 2012.

(Continued)

*Primary Examiner* — Cris L Rodriguez
*Assistant Examiner* — Hao D Mai
(74) *Attorney, Agent, or Firm* — Nixon Peabody LLP

(57) ABSTRACT

An orthodontic connection tool for attaching to a screw that has been embedded in a bone in the oral cavity an upper structural body to which an orthodontic tool is fixed, the orthodontic connection tool being provided with a base plate that is engageable with the screw; and a structural body fixture that is engaged with the base plate at an arbitrary position thereof and that fixes the upper structural body in a detachable manner.

3 Claims, 19 Drawing Sheets

(56) References Cited

U.S. PATENT DOCUMENTS

| | | |
|---|---|---|
| 2004/0166461 A1 | 8/2004 | DeVincenzo |
| 2006/0223029 A1* | 10/2006 | Berger .......................... 433/172 |
| 2006/0257811 A1* | 11/2006 | Ohki et al. ...................... 433/18 |
| 2006/0293673 A1* | 12/2006 | Morrison et al. ................ 606/69 |
| 2008/0124675 A1* | 5/2008 | Adams .......................... 433/174 |
| 2009/0204121 A1* | 8/2009 | Cavallazzi et al. .............. 606/96 |
| 2011/0053109 A1* | 3/2011 | Zipprich et al. ................ 433/18 |

FOREIGN PATENT DOCUMENTS

| | | |
|---|---|---|
| JP | 2004-057729 A | 2/2004 |
| JP | 2005-185705 A | 7/2005 |
| JP | 2007-097987 A | 4/2007 |
| JP | 2008-183016 A | 8/2008 |
| WO | WO 2008090979 A1 * | 7/2008 |

OTHER PUBLICATIONS

Office Action in Japanese Application No. 2011-006980, mailed Dec. 2, 2014.

Notice of Allowance in Japanese Patent Application No. 2011-006980, mailed Apr. 24, 2015.

Office Action in Chinese Patent Application No. 201280005412.3, issued May 14, 2015.

* cited by examiner

ORTHODONTIC CONNECTION TOOL

CROSS REFERENCE TO RELATED APPLICATIONS or PRIORITY CLAIM

This application is a National Phase of PCT/JP2012/050810, filed Jan. 17, 2012, entitled, "ORTHODONTIC CONNECTION TOOL", which claims the benefit of Japanese Patent Application No. 2011-006980, filed Jan. 17, 2011, the contents of which are incorporated herein by reference in their entirety.

TECHNICAL FIELD

The present invention relates to an orthodontic connection tool that, for performing correction that causes teeth to move with screws embedded in a bone in the oral cavity serving as an anchorage, connects an upper structural body and the screws.

BACKGROUND ART

In conventional orthodontics, there is an orthodontic method that involves connecting a tooth that is fixed and a tooth that is to be straightened (tooth to be moved), and pulling and moving the tooth to be straightened with the fixed tooth serving as an axis. In this case, since the two teeth are pulled toward each other, the fixed tooth may move toward the tooth to be moved. Therefore, an orthodontic treatment is performed that involves embedding and fixing in the bone of the jaw a screw-type implant in which for example a cylindrically shaped screw portion is formed, fixing an upper structural body such as a plate or wire to this screw with a fixing means such as brazing, and directly or indirectly fixing the upper structural body to a tooth (for example, refer to Patent Document 1).

Patent Document 1 discloses an implant structure in which an anchor head in which a slot is provided is fixed to the head portion of the implant body, with a screw hole that penetrates this anchor head being provided in the vertical direction. In this implant structure, the implant body (corresponding to a screw) is fixed by being embedded in the jaw bone, a wire having one end thereof fixed to a tooth is engaged in the slot, and by threadably mounting a screw into the screw hole, the wire is fixed by the distal end portion of that screw.

PRIOR ART DOCUMENTS

Patent Document

Patent Document 1:
Japanese Unexamined Patent Application, First Publication No. 2004-57729

However, the conventional implant structure has the following problems.

Conventionally, an upper structural body such as a plate is fixed to a screw that is embedded in a bone by a fixing means such as brazing, or as shown in Patent Document 1, a wire is fixed by a screw to the screw that is embedded in the bone. For that reason, in the case of wanting to change the position of the screw that serves as the anchorage, or in the case of performing teeth straightening by swapping with an upper structural body having a different shape, the screw that is once embedded must be extracted, and a new screw must be embedded at the desired location. For that reason, it is not possible to easily alter the upper structural body. In addition, since a structure that enables attachment and detachment of the upper structural body to/from the screw is complicated, the manufacturing cost is high.

The object of the present invention, conceived in view of the above problems, is to provide an orthodontic connection tool that can enable an upper structural body to be easily attached and detached without changing the position of the screw, and that can allow the position and number of the upper structural body to be easily changed. Also, another object of the present invention is to provide an orthodontic connection tool that enables a reduction in manufacturing cost by having a simple structure.

DISCLOSURE OF THE INVENTION

In order to attain the aforementioned objects, the present invention adopts the following means. The orthodontic connection tool according to the present invention is an orthodontic connection tool for attaching to a screw that has been embedded in a bone in the oral cavity an upper structural body to which an orthodontic tool is fixed, the orthodontic connection tool being provided with: a base plate that is engageable with the screw; and a structural body fixture that is engaged with the base plate at an arbitrary position thereof and that fixes the upper structural body in a detachable manner.

In the present invention, in the case of performing a procedure that involves arranging in the oral cavity an upper structural body that is an implant structure used for straightening teeth, a base plate is fixed in the oral cavity by screws that are embedded in a bone in the oral cavity, and a structural body fixture is engaged with a predetermined position of that base plate. Thereby, the connection tool is arranged, and it is possible to attach the upper structural body to the structural body fixture. That is to say, it is possible to attach the structural body fixture, which becomes the attachment position of the upper structural body, to an arbitrary position of the base plate. Thereby, it is possible to readily attach and detach the upper structural body without changing the positions of the screws, and it is also possible to easily perform changes to the position and number of the upper structural body. In this way, since a simple detachable structure results that does not require work such as redriving the screws into different positions, it is possible to reduce manufacturing costs.

Also, in the orthodontic connection tool according to the present invention, it is preferable that the upper structural body have a fitting hole that has a concavo-convex portion along the inner periphery; and the structural body fixture have a fitting convex portion that has a concavo-convex portion on the outer periphery that fits the fitting hole.

In this case, the inner peripheral concavo-convex surface of the upper structural body is capable of engaging with the outer peripheral concavo-convex surface of the structural body fixture in any direction in a rotative direction centered on the central axial line of the fitting hole. Thereby, it is possible to change the orientation (rotation angle) of the upper structural body to face an arbitrary direction.

Also, in the orthodontic connection tool according to the present invention, it is preferable that the screw have an angular head portion in which the cross-sectional shape perpendicular to the screw axial direction is a polygonal shape; the base plate have a plurality of angular locking holes arrayed that engage the angular head portion of the screw; and the structural body fixture have an angular engaging portion that engages the angular locking hole from the upper surface side of the base plate.

In this case, another angular locking hole in which one screw is not engaged is suitably selected from among the plurality of angular locking holes of the base plate, and it is possible to cause the angular engaging portion to engage with that selected angular locking hole. Thereby, the structural body fixture is fixed, and moreover it is possible to attach the upper structural body to that structural body fixture. In this case, since engaging portions of the angular head portion of the screw and the angular locking hole of the base plate mutually have angular shapes, the screw and the base plate are fixed in the state of rotation of the base plate being restricted with respect to the screw. Moreover, since the angular engaging portion of the structural body fixture is engaged in the angular locking hole of the base plate, a simple detachable structure results in which there is no need to redrive the screw into a different position. For that reason, by causing the structural body fixture to be engaged in another angular locking hole, it is possible to easily change the position and number of the upper structural body.

Also, the number of angular locking holes in the base plate can be arbitrarily set. That is to say, by using the plurality of other angular locking holes in which the angular head portion of the one screw is not engaged, it is possible to attach a plurality of structural body fixtures to a single base plate. For that reason, it is possible to favorably arrange a plurality of the upper structural bodies in the oral cavity, and there is no need to embed in a bone more than the required number of screws in order to fix a plurality of the upper structural bodies. Also, since the angular head portion of the screw and the angular engaging portion of the structural body fixture have the same shape, the plurality of the angular locking holes that are provided in the base plate are in common with the angular head portion and the angular engaging portion. For that reason, since a simple structure results, manufacturing is simplified and it is possible to reduce manufacturing costs.

Also, in the orthodontic connection tool according to the present invention, it is preferable that the base plate be elongated, the structural body fixture be engaged at an arbitrary position of the base plate in the lengthwise direction, and the angular locking hole that is positioned at one end side in the lengthwise direction among the plurality of angular locking holes be a locking oblong hole that is long in the lengthwise direction.

In this case, when embedding two screws in a bone in the oral cavity having a predetermined mutual distance, provided the interval of the two screws is less than or equal to a predetermined distance, when one screw is engaged in any one of the plurality of angular locking holes, it is always possible to cause the other screw to be engaged in the locking oblong hole. Thereby, it is possible to fix the base plate to a bone in the oral cavity. This predetermined distance denotes the interval of the two screws in the case of the angular head portion of one screw being engaged in the angular locking hole that is positioned furthest away from the locking oblong hole of the base plate, and the angular head portion of the other screw being engaged in the locking oblong hole at a position within the inner periphery farthest away from the one screw. That is to say, provided the interval of the two screws is equal to or less than a predetermined interval, it is possible to embed the two screws in a bone regardless of their mutual interval. Thereby, high precision positioning during embedding of the screws becomes unnecessary, and the work becomes more efficient.

Also, in the orthodontic connection tool according to the present invention, it is preferable that the structural body fixture have a locking member that restricts movement of this angular engaging portion in the direction of slipping out with respect to the angular locking hole. In this case, in the state of the angular engaging portion being engaged in the angular locking hole, it is possible to reliably fix the structural body fixture and the base plate by the locking means.

Also, in the orthodontic connection tool according to the present invention, it is preferable that the locking means be a holding member that grasps the base member from the lateral surface sides thereof. In this case, since for example the holding member that imparts a biasing force grasps the base plate from the lateral surface sides thereof, it is possible to restrict movement in which the structural body fixture moves upward so as to reliably fix the structural body fixture and the base plate.

Also, in the orthodontic connection tool according to the present invention, it is preferable that the structural body fixture be cylindrical and have a female thread portion that is formed in the inner periphery; the locking member have slits that extend upward in the vertical direction from the lower end of the angular engaging portion, and a male screw that is threadably mounted in the female thread portion; and in the state of the male screw being threadably mounted in the female thread portion, the angular engaging portion expand in diameter. In this case, in the state of the male screw not being threadably mounted in the female thread portion, the angular engaging portion has a reduced diameter toward the center side in the radial direction to an extent enabling passage through the angular locking hole of the base plate, and in the state of the angular engaging portion being engaged in the angular locking hole, when the male screw is threadably mounted in the female thread portion, the angular engaging portion that is partitioned by the slits expands outward in the radial direction. At this time, since the angular engaging portion is locked in the state of abutting the inner surface of the angular locking hole, it is possible to restrict movement in which the structural body fixture moves upward so as to reliably fix the structural body fixture and the base plate.

Also, in the orthodontic connection tool according to the present invention, it is preferable that the locking member be a wire that is wound in an integrated manner around the base plate and the structural body fixture. In this case, since the base plate and the structural body fixture are wound in an integrated manner by the wire, it is possible to restrict movement in which the structural body fixture moves upward so as to reliably fix the structural body fixture and the base plate.

Effects of the Invention

The orthodontic connection tool of the present invention is a simple structure that just causes the angular head portion of a screw and the angular engaging portion of a structural body fixture to be engaged in suitable positions selected among a plurality of angular locking holes, and so it is possible to easily attach and detach an upper structural body. Also, modification of the mounting position and number of the structural body fixture with respect to the base plate can also be easily performed without changing the position of the screw. Moreover, since it is a simple structure in which a plurality of the angular locking holes that are in common with the angular head portion of the screw and the angular engaging portion of the structural body fixture are provided in the base plate, it is possible to reduce manufacturing costs.

BEST MODE FOR CARRYING OUT THE INVENTION

Hereinbelow, an orthodontic connection tool according to embodiments of the present invention shall be described based on the drawings.

First Embodiment

Figure 1:
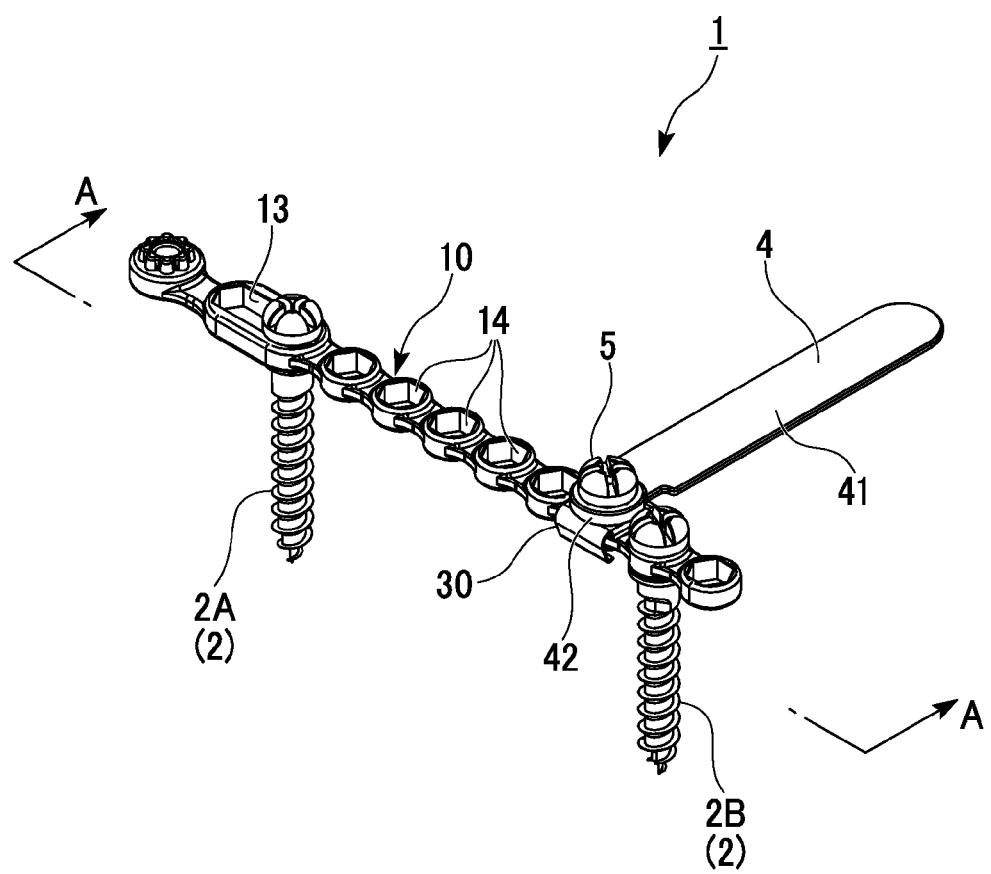
FIG. 1 is a perspective drawing that shows the entire constitution of an implant structure according to the first embodiment of the present invention.

A connection tool 10 according to the first embodiment shown in FIG. 1 is adopted as a portion of an implant structure 1 that is used in straightening teeth, and connects a pair of screws 2 (2A, 2B) that are fixed by being embedded in the bone of the jaw in the oral cavity, and an upper structural body 4 that is arranged in the oral cavity. This implant structure 1 is used for performing such procedures as moving teeth in a desired direction by affixing an orthodontic bracket or the like not shown to the upper structural body 4 by brazing or the like, and moreover connecting the implant structure 1 to predetermined teeth via orthodontic tools such as orthodontic wire, elastic, springs and the like. That is to say, the connection tool 10 is a member for fixing an orthodontic tool to the bone of the jaw portion. Here, throughout the description of the implant structure 1 that is arranged in the oral cavity, the bone side shall be referred to as the lower side while the opposite side shall be referred to as the upper side.

As shown in FIG. 1 to FIG. 5, the upper structural body 4 has a plate main body 41 that has an elongated thin plate shape, and a fitting hole 42 that penetrates in the thickness direction one end of this plate main body 41 in the lengthwise direction. A concavo-convex portion that fits with a first fitting projection portion 12 and a second fitting projection portion 31 described later is formed over the circumference of the inner periphery of this fitting hole 42. Note that the upper structural body 4 is constituted from a material such as stainless steel that is capable of brazing.

Figure 6A:
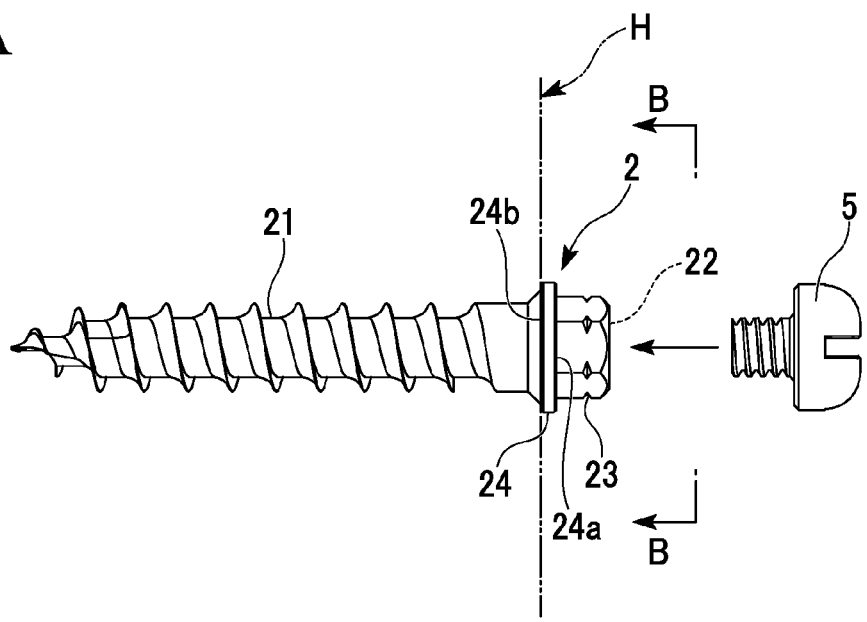
FIG. 6A is a side view that shows the screw and the male screw that is attached to this screw.
Figure 6B:
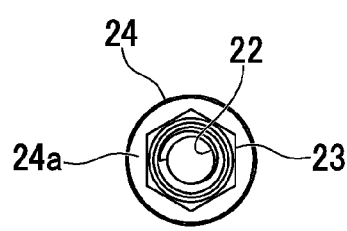
FIG. 6B is an arrow view from the line B-B shown in FIG. 6A.

The pair of screws 2A, 2B are made of a material such as titanium or a titanium alloy or the like, and are arranged in a state of being embedded in the jaw bone so as to be approximately parallel while separated by a predetermined distance from each other. Specifically, the screw 2, as shown in FIG. 6A and FIG. 6B, has a male thread portion 21, a female thread portion 22 that is provided at the end face of the head portion side, a hexagonal head portion 23 (angular head portion) in which the cross-sectional shape perpendicular to the axial direction forms a hexagonal shape at the head portion, and a locking ring 24 that is coaxial with the screw axis and provided at the distal end side of the hexagonal head portion 23. The hexagonal head portion 23 is arranged at a position making contact with the base end side surface (upper surface 24a) of the locking ring 24. Note that when the two screws 2A, 2B are in the state of being embedded in the bone of the jaw portion separated by a predetermined distance from each other, the two screws 2A and 2B need not be in a mutually parallel state.

The male thread portion 21 is provided with a cylindrical main body that forms an acuminate shape at the lower end, and a spiral ridge portion that is formed on this main body over the entire axial direction. The screw 2 is embedded in the bone of the jaw portion by rotating this male thread portion 21. At this time, the locking ring 24 is fixed contacting the surface of the bone (mucous), and the portion upward from the locking ring 24 is exposed to the oral cavity.

The locking ring 24 has a ring shape, and is provided over the entire circumference of the screw 2 in the circumferential direction. As shown in FIG. 6B, the outer diameter of this locking ring 24 is larger than the outer diameter of the hexagonal head portion 23. That is to say, in the state of the hexagonal head portion 23 being engaged in a locking oblong hole 13 or a hexagonal locking hole 14 of the base plate 11 described below, the upper surface 24a of the locking ring 24 contacts the lower surface 11b of the base plate 11, and the male screw 5 is threadably mounted from the upper side of the base plate 11 into the female thread portion 22.

As shown in FIG. 1 and FIG. 7 to FIG. 10, the connection tool 10 is provided with the base plate 11 in which the attachment of the two screws 2A, 2B is possible, regardless of the distance between the screw 2A and the screw 2B that are fixed in the jaw, and a structural body fixture 30 that is provided at a predetermined position on the upper side of the base plate 11 for the purpose of fixing the upper structural body 4.

The base plate 11 is formed from a material such as stainless steel or titanium, and is provided with the first fitting projection portion 12 that is provided at one end in the lengthwise direction and engages in the fitting hole 42 of the upper structural body 4, the locking oblong hole 13 (oblong hole-shaped through-hole) that is provided at the other end side in the lengthwise direction of this first fitting projection portion 12, and a plurality (here, eight) of hexagonal locking holes 14, 14, . . . (angular locking holes) that are arranged at an equal interval from this locking oblong hole 13 to the other end side in the lengthwise direction.

The first fitting projection portion 12 fits in the aforementioned fitting hole 42 of the upper structural body 4, and a concavo-convex portion corresponding to the fitting hole 42 is formed over the entire circumference of the outer periphery thereof. That is to say, the outer periphery of the first fitting projection portion 12 can mesh in a freely rotating manner in a rotation direction centered on the center axis line of the fitting hole 42 at an arbitrary position in the inner periphery of the fitting hole 42. Thereby, it is possible to attach the upper structural body 4 to the first fitting projection portion 12 with the orientation (rotation angle) of the upper structural body 4 altered.

The first fitting projection portion 12 is provided with a female thread portion 12a that is formed so as to penetrate the base plate 11 in the thickness direction, and with which the male screw 5 (refer to FIG. 2) is threadably mounted. That is to say, it is possible to fix the upper structural body 4 to the base plate 11 by threadably mounting the male screw 5 in the female thread portion 12a, in the state of the first fitting projection portion 12 being fitted in the fitting hole 42, and the upper structural body 4 being attached to the base plate 11.

The hexagonal locking hole 14 is provided with a hexagonally shaped inner periphery that is capable of engaging with the hexagonal head portion 23 of the screw 2. The locking oblong hole 13 is provided with a hexagonally shaped inner periphery in which the sides that extend parallel to the lengthwise direction of the base plate 11 are long. That is to say, the base plate 11 can be installed in conformity with the interval of the pair of screws 2A and 2B. Specifically, provided the interval of the pair of screws 2A and 2B is less than or equal to a predetermined distance (that is, the distance between the two screws 2 when one screw 2 is engaged in the hexagonal locking hole 14 positioned furthest away from the locking oblong hole 13, and the other screw 2 is engaged in the locking oblong hole 13 nearer the first fitting projection portion 12), when the one screw 2 (here, reference numeral 2B) is engaged in any one of the plurality of hexagonal locking holes 14, it is always possible to cause the other screw to be engaged in the locking oblong hole 13. That is to say, provided the interval of the pair of screws 2A, 2B is less than or equal to the predetermined distance, it is possible to embed the pair of screws 2A, 2B regardless of the interval between the two.

As shown in FIG. 11 to FIG. 15, the structural body fixture 30 is provided with a second fitting projection portion 31, a substrate portion 32, a hexagonal engaging portion 33 (angular engaging portion), and a spring member 35 (locking member, holding member). The second fitting projection portion 31, the substrate portion 32, and the hexagonal engaging portion 33 (angular engaging portion) are arranged in sequence along the axial line direction (the vertical direction in the state of being attached to the base plate 11). A hole extending in the axial line direction that is provided with an inner periphery thereof in which a female thread portion 34 is formed is provided in the second fitting projection portion 31, the substrate portion 32, and the hexagonal engaging portion 33. Moreover, the spring member 35 (locking member, holding member) that locks with the base plate 11 (refer to FIG. 12) is provided on the upper face of the substrate portion 32.

Here, the second fitting projection portion 31, the substrate portion 32, and the hexagonal engaging portion 33 are arranged in the state of their respective center axis lines being positioned on a common single axis. In this embodiment, the common axis is denoted as center axis O, and in the structural body fixture 30, the second fitting portion 31 side along the center axis O with respect to the substrate portion 32 shall be referred to as the upper side, and the hexagonal engaging portion 33 side shall be referred to as the lower side. Also, the direction perpendicular to the center axis O shall be the diameter direction.

The second fitting projection portion 31 engages in the fitting hole 42 of the upper structural body 4, and a concavo-convex portion corresponding to the aforementioned fitting hole 42 is formed along the entire circumference of the outer periphery of the second fitting projection portion 31, in the same manner as the aforementioned first fitting projection portion 12. That is to say, since the concavo-convex portion of the fitting hole 42 and the concavo-convex portion of the second fitting projection portion 31 are capable of meshing at an arbitrary position, attachment can be performed with the orientation (rotation angle) of the upper structural body 4 with respect to the second fitting projection portion 31 altered.

The substrate portion 32 has an approximately square shape that is larger than the second fitting projection portion 31 and the hexagonal engaging portion 33 in plan view perpendicular to the center axis O direction. The hexagonal engaging portion 33 is capable of engaging in each of the plurality of hexagonal locking holes 14 of the base plate 11, and the cross-sectional shape perpendicular to the center axis O is hexagonal. Also, the male screw 5 is threadably mounted in the female thread portion 34. The upper structural body 4 is fixed by threadably mounting the male screw 5 in the female thread portion 34, in the state of the fitting hole 42 of the upper structural body 4 being engaged on the second fitting projection portion 31.

The spring member 35 that is shown in FIG. 11, FIG. 12 and FIG. 15 to FIG. 17 is placed on the upper surface of the substrate portion 32 so as to wrap around the base plate 11, and is provided with a fixing curled portion 35a that locks with edge portions of two opposing sides of the substrate portion 32, a spring main body 35b that is curved downward from both edges of the other opposing two sides and extended downward, and a claw portion 35c that is bent toward the center axis O side at the lower end thereof.

Figure 2:
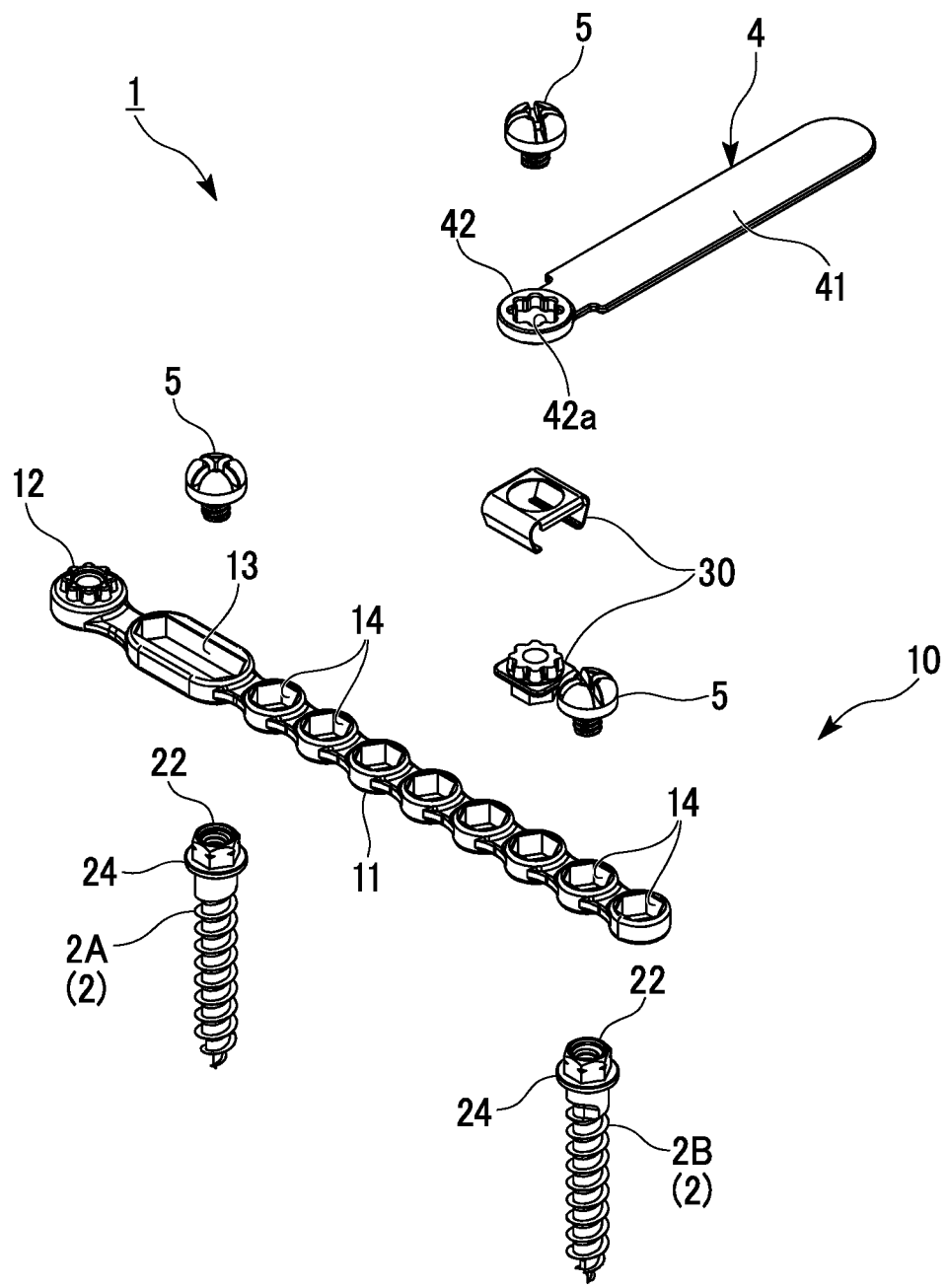
FIG. 2 is an exploded perspective drawing of the implant structure shown in FIG. 1.
Figure 3:
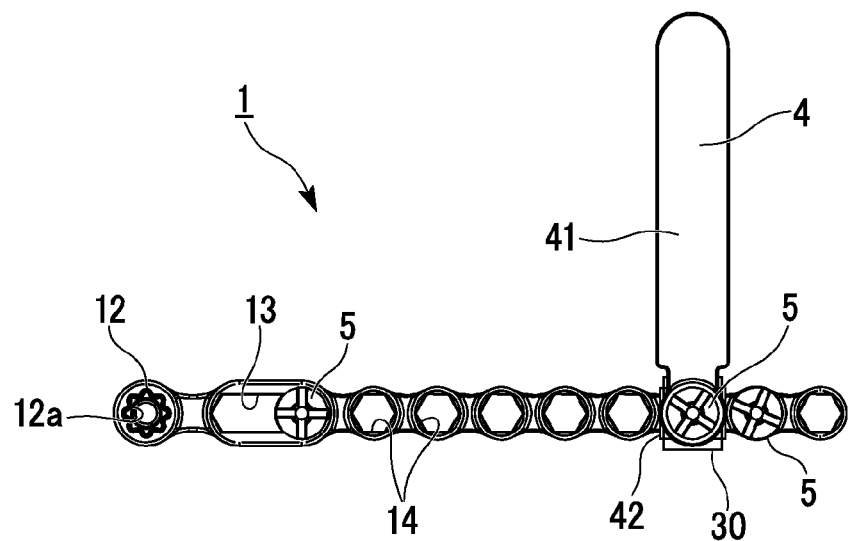
FIG. 3 is a top view of the implant structure shown in FIG. 1.
Figure 4:
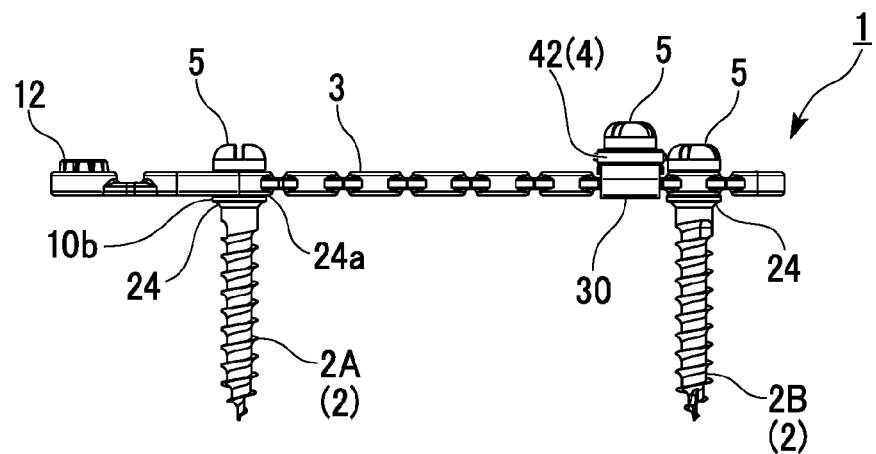
FIG. 4 is a side view of the implant structure, being an arrow view from the line A-A shown in FIG. 1.
Figure 5:
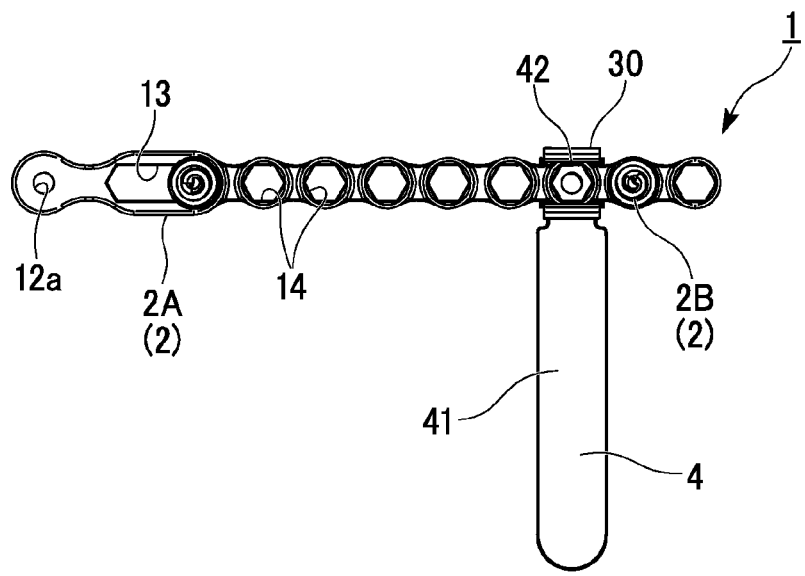
FIG. 5 is a bottom view of the implant structure shown in FIG. 1.
Figure 7:
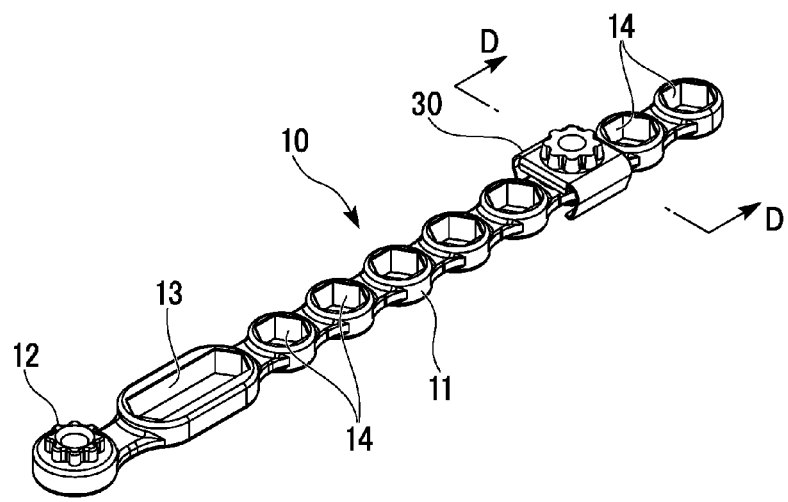
FIG. 7 is a perspective view that shows the entire constitution of the connection tool, being a drawing that omits the upper structural body in FIG. 1.

In this structural body fixture 30, as shown in FIG. 1 and FIG. 2, in the state of the hexagonal engaging portion 33 having been engaged in any of the plurality of hexagonal locking holes 14, 14, . . . from the upper surface 11a side of the base plate 11, the spring member 35 locks with the lower surface 11b of the base plate 11 with the claw portions 35c, 35c by means of the bias of the spring, while gripping the base plate 11 from the width direction with the pair of spring main bodies 35b, 35b (refer to FIG. 7).

Next, the installation method of the implant structure 1 using the connection tool 10 mentioned above and the action of the connection tool 10 shall be described with reference to the drawings. As shown in FIG. 1, first, an anchor position of the implant structure 1 (that is, the embedding position of the screws 2A, 2B) is determined with respect to the jawbone in the oral cavity of the patient having to undergo teeth straightening (for example, the central part of the palatal bone of the upper jaw). A special-purpose driver (not illustrated) is used to embed the two screws 2A, 2B while rotating them so as to be parallel with a predetermined mutual distance. Note that the embedding position of the screws 2 shall be the position at which the lower surface 24b of the locking ring 24 makes contact with the surface of the membrane (the chain double-dashed line H shown in FIG. 6). At this time, since the locking ring 24 is in a state of contacting the surface H of the membrane, it is possible to prevent the screws 2A, 2B from sinking into the membrane. Note that when embedding the two screws 2A, 2B while rotating them with a predetermined mutual distance, the two screws 2A, 2B need not be in a mutually parallel state.

Next, as shown in FIG. 1 to FIG. 5, the base plate 11 of the connection tool 10 is fixed to the two screws 2A, 2B that have been embedded. Specifically, provided the interval of the two screws 2A, 2B is less than or equal to a predetermined distance, when the one screw 2B has been engaged in any one of the plurality of hexagonal locking holes 14, it is always possible to engage the other screw 2A in the locking oblong hole 13. Thereby, it is possible to fix the base plate 11 in the bone of the oral cavity. This predetermined distance denotes the interval of the two screws in the case of the hexagonal head portion 23 of one screw 2 (here, reference numeral 2B) being engaged in the hexagonal locking hole 14 that is positioned furthest away from the locking oblong hole 13 of the base plate 11, and the hexagonal head portion 23 of the other screw 2 (here, reference numeral 2A) being engaged in the locking oblong hole 13 at a position within the inner periphery farthest away from the one screw 2B. Then, as shown in FIG. 6A, by threadably mounting the male screws 5 in the female thread portions 22 of the screws 2A, 2B, the screws 2A, 2B and the base plate 11 are fixed. That is to say, provided the two screws 2A, 2B are equal to or less than a predetermined interval, regardless of their mutual interval, it is possible to embed the two screws 2A, 2B. Thereby, high precision positioning during embedding of the screws 2A, 2B becomes unnecessary, and the work can be made more efficient. Also, since the engaging portion of each screw 2 and the base plate 11 (the hexagonal head portion 23, the hexagonal locking hole 14, respectively) are mutually angular shapes, they are fixed in the state of rotation of the screw 2 being restricted with respect to the base plate 11.

Figure 8:
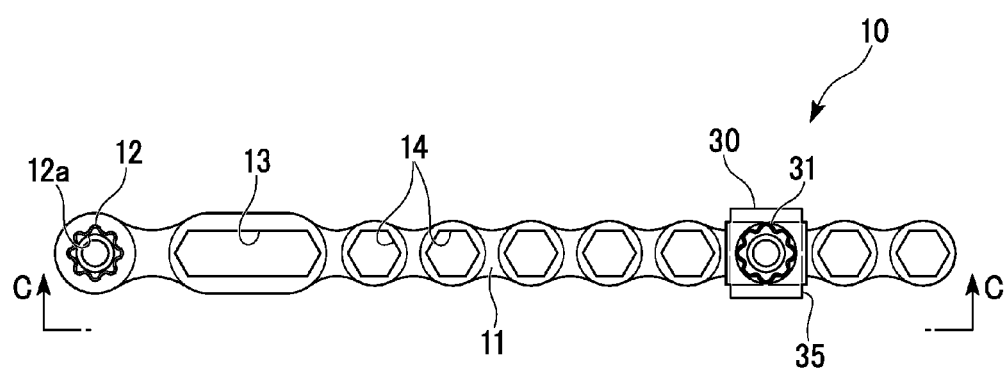
FIG. 8 is a top view of the connection tool shown in FIG. 7.
Figure 9:
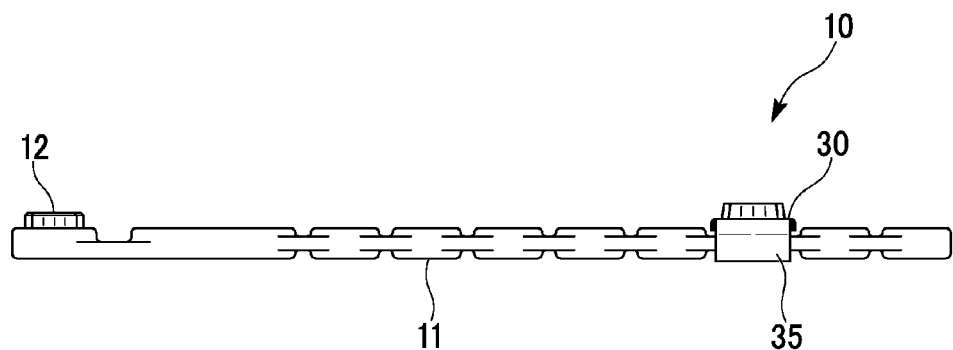
FIG. 9 is a side view of the connection tool, being an arrow view from the line C-C shown in FIG. 8.
Figure 10:
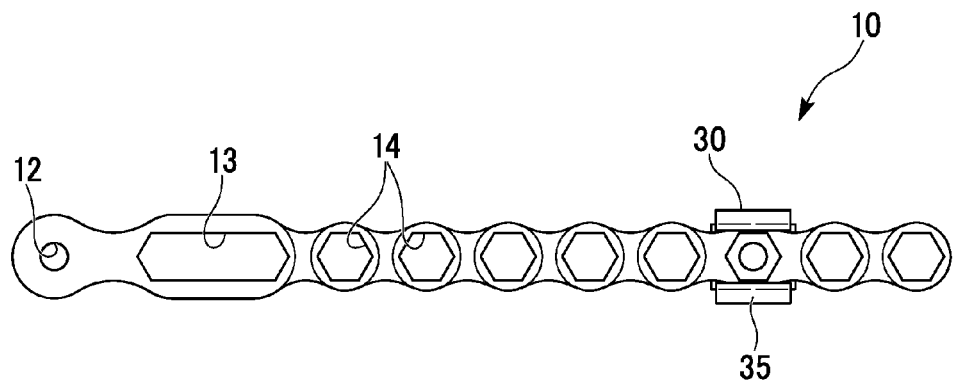
FIG. 10 is a bottom view of the connection tool shown in FIG. 7.
Figure 11:
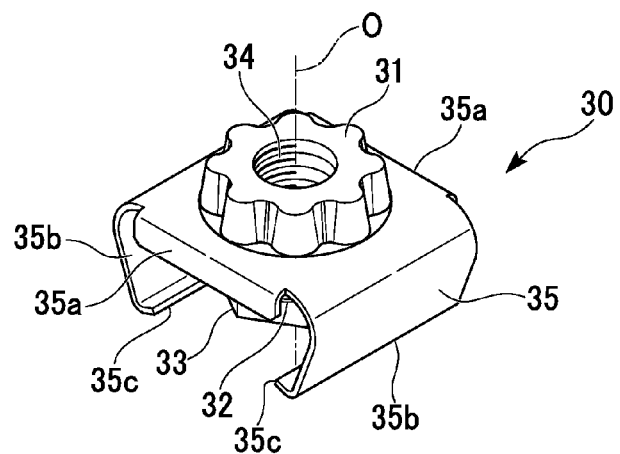
FIG. 11 is a perspective view that shows the entire constitution of the structural body fixture.
Figure 12:
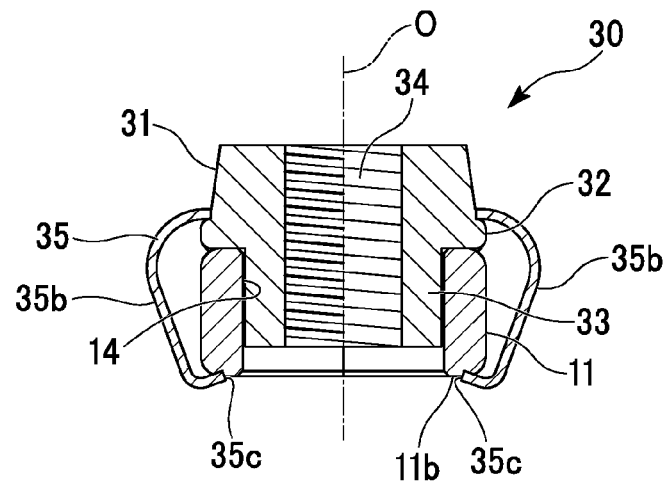
FIG. 12 is a cross-sectional view along the line D-D shown in FIG. 7.
Figure 13:
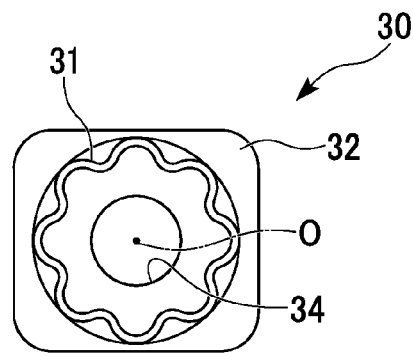
FIG. 13 is a top view of the structural body fixture, being a drawing that omits the spring member.
Figure 14:
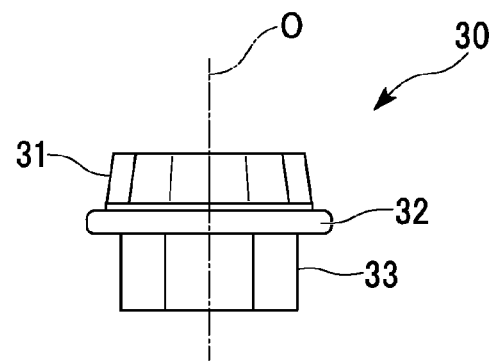
FIG. 14 is a side view of the structural body fixture, being a drawing that omits the spring member.
Figure 15:
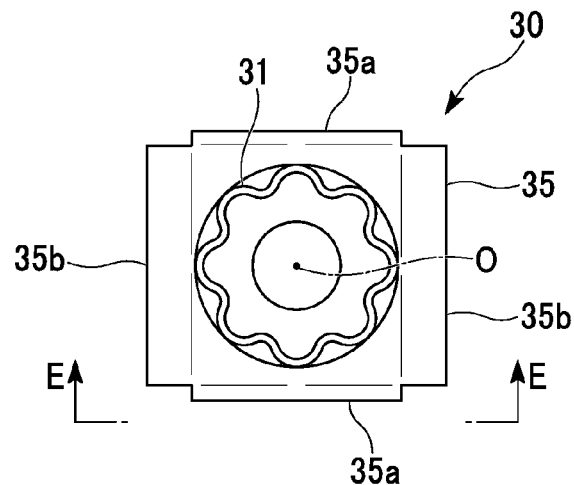
FIG. 15 is a top view of the structural body fixture.
Figure 16:
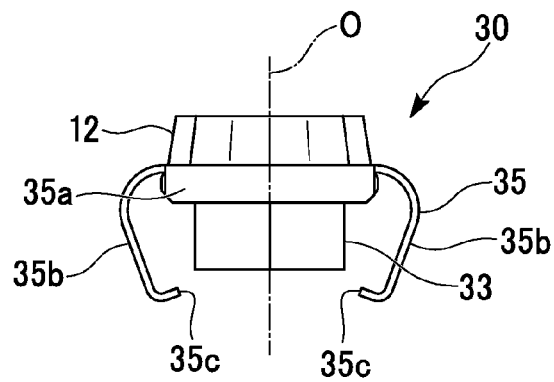
FIG. 16 is an arrow view from the line E-E shown in FIG. 15.
Figure 17:
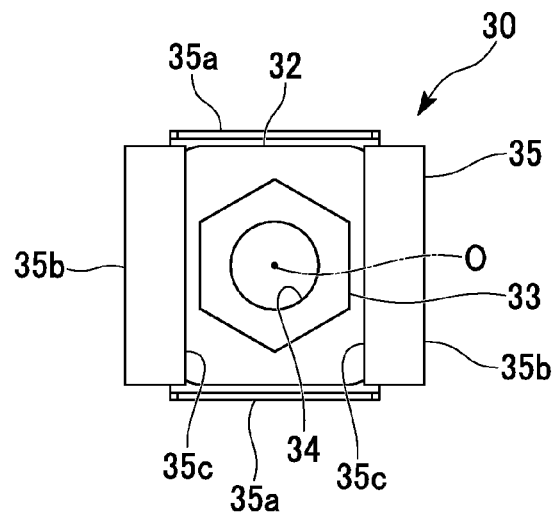
FIG. 17 is a bottom view of the structural body fixture.

Next, as shown in FIG. 8 to FIG. 10, the structural body fixture 30 is attached at a suitable location among the plurality of hexagonal locking holes 14, 14 of the base plate 11. That is to say, in the structural body fixture 30, the hexagonal engaging portion 33 is engaged in the predetermined hexagonal locking hole 14 while positioning both spring main bodies 35b, 35b of the locking spring 35 shown in FIG. 11 and FIG. 12 on the outside of the base plate 11 while spreading them apart toward the outside in the radial direction in opposition to the bias. Then, when the lower surface 32a of the substrate portion 32 contacts the upper surface 11a of the base plate 11, the claw portions 35c of the locking spring 35 lock with the lower surface 11b of the base plate 11 by the bias of the spring main bodies 35b. Thereby, the structural body fixture 30 is reliably fixed to the base plate 11.

Next, after the fitting hole 42 of the upper structural body 4 is inserted on the second fitting projection portion 31 of the structural body fixture 30, by threadably mounting the male screw 5 in the female thread portion 34, the upper structural body 4 is fixed to the base plate 11. At this time, since the fitting hole 42 of the upper structural body 4 and the second fitting projection portion 31 are meshed together by the mutual concavo-convex portions, rotation centered on the second fitting projection portion 31 of the upper structural body 4 with respect to the structural body fixture 30 is restricted.

Note that in the present connection tool 10, it is also possible to attach the upper structural body 4 to the first fitting projection portion 12 of the base plate 11. In this case, after inserting the fitting hole 42 of the upper structural body 4 on the first fitting projection portion 12, the male screw 5 is threadably mounted in the female thread portion 12a.

In this way, another hexagonal locking hole 14 in which the one screw 2B is not engaged is suitably selected from among the plurality of hexagonal locking holes 14, 14, . . . of the base plate 11 that is fixed to the bone, and the hexagonal engaging portion 33 is engaged with the selected hexagonal locking hole 14. Thereby, the connection tool 10 comes to be arranged by the structural body fixture 30 being fixed to the base plate 11, whereby it is possible to attach the upper structural body 4 to the structural body fixture 30.

Also, the hexagonal head portion 23 of the screw 2 and the hexagonal engaging portion 33 of the structural body fixture 30 have the same shape, and the plurality of hexagonal locking holes 14 that are provided in the baseplate 11 are in common with the hexagonal head portion 23 and the hexagonal engaging portion 33. For that reason, it has a simple structure, and so manufacturing becomes easy and it is possible to reduce manufacturing costs. Also, since the hexagonal engaging portion 33 of the structural body fixture 30 is engaged in the hexagonal locking hole 14 of the base plate 11, a simple detachable structure results that does not require work such as redriving the screw 2 into a different position. For that reason, by engaging the structural body fixture 30 at a different hexagonal locking hole 14, it is possible to easily change the position of the upper structural body 4.

Moreover, it is possible to arbitrarily set the number of the hexagonal locking holes 14 in the base plate 11. That is to say, it is possible to attach a plurality of structural body fixtures 30 to a single base plate 11 by using the plurality of other hexagonal locking holes 14 in which the hexagonal head portion 23 of the one screw 2B is not engaged. For that reason, it is possible to favorably arrange a plurality of the upper structural bodies 4 in an oral cavity, and so in order to fix a plurality of the upper structural bodies 4 the need to embed in a bone more than the required number of the screws 2 is eliminated.

The orthodontic connection tool according to the embodiment as given above is a simple structure that just causes the hexagonal head portions 23 of the screws 2 and the hexagonal engaging portion 33 of the structural body fixture 30 to be engaged in suitable positions selected among the plurality of hexagonal locking holes 14. For that reason, it is possible to easily attach and detach the upper structural body 4, and changing the attachment position and number of the structural body fixture 30 with respect to the base plate 11 can be easily performed without changing the position of the screws 2. Also, by adopting a simple structure that provides a plurality of the hexagonal locking holes 14 that are in common with the hexagonal head portion 23 of the screw 2 and the hexagonal engaging portion 33 of the structural body fixture 30, it is possible to reduce the manufacturing cost.

Next, other embodiments and modifications of the orthodontic connection tool of the present invention shall be described referring to the drawings. Note that those components and portions that are the same or similar as those of the first embodiment given above shall be denoted by the same reference numerals with their descriptions omitted, while constitutions differing from the first embodiment shall be described. For example, in the other embodiments given below, the constitutions of the screw 2, the upper structural body 4, and the base plate 11 are the same as in the first embodiment, so detailed descriptions thereof shall be omitted.

Second Embodiment

Figure 18:
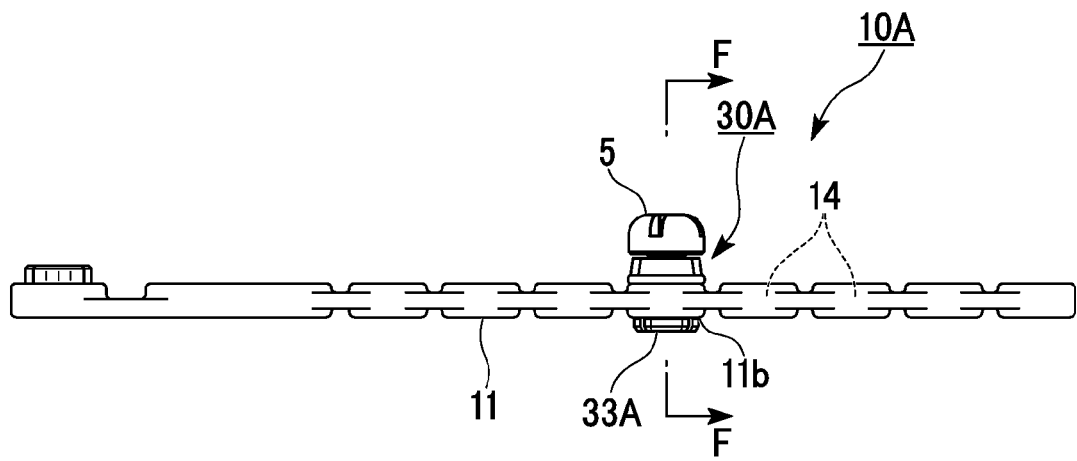
FIG. 18 is a side view that shows the entire constitution of the connection tool according to the second embodiment.

The orthodontic connection tool 10A according to the second embodiment shown in FIG. 18 is one in which the spring member 35 is omitted in the structural body fixture 30 of the aforementioned first embodiment, while the constitution of the hexagonal engaging portion 33 (refer to FIG. 8 and the like) is replaced.

As shown in FIG. 18 to FIG. 21, in a hexagonal engaging portion 33A of a structural body fixture 30A in the second embodiment, a plurality (here, three) of slits 33a are provided that project further downward than the lower surface 11b of the base plate 11, and extend from the bottom end upward, in the state of the structural body fixture 30A being engaged in the hexagonal locking hole 14 of the base plate 11. Moreover, the outer periphery of the hexagonal engaging portion 33A forms a bulging portion 33b (locking member) in which the lower end side portion bulges further outward to the outside in the radial direction than the trunk portion 33c. The female thread portion 34 (refer to FIG. 19) is formed over the entire structural body fixture 30A in the vertical direction.

Figure 19:
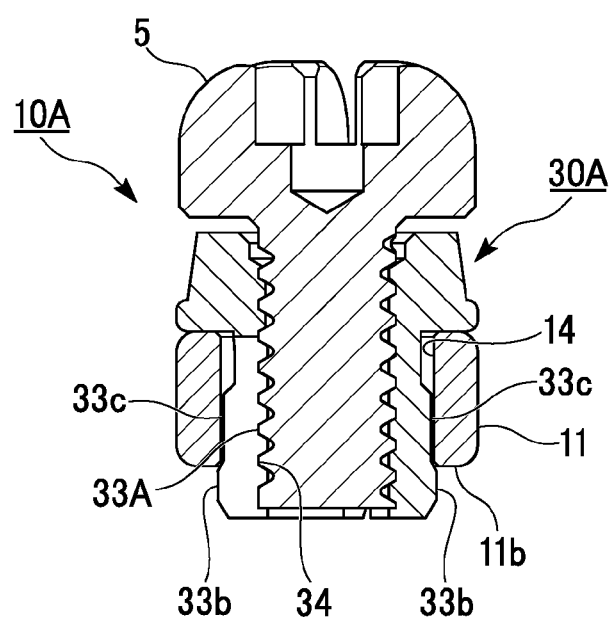
FIG. 19 is a cross-sectional view along the line F-F shown in FIG. 18.
Figure 20:
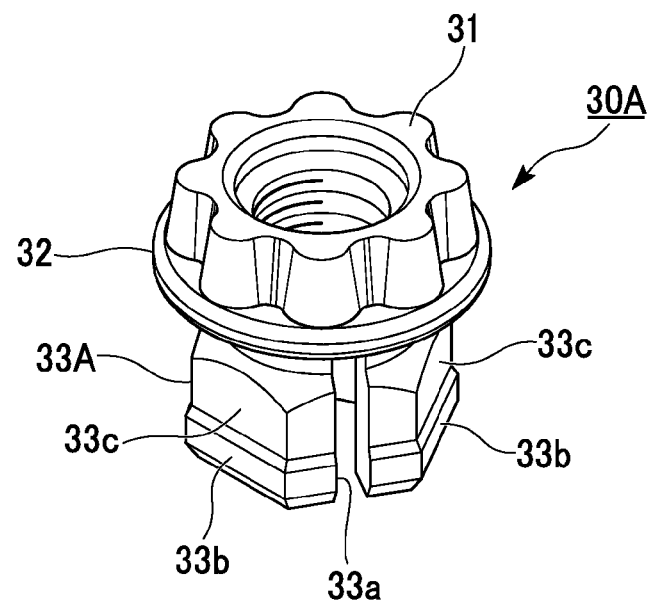
FIG. 20 is a perspective view that shows the entire constitution of the structural body fixture.
Figure 21:
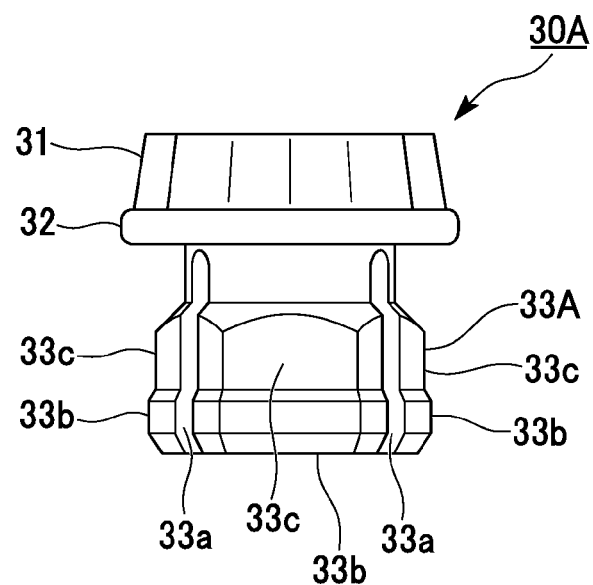
FIG. 21 is a side view of the structural body fixture.

With this kind of hexagonal engaging portion 33A, as shown in FIG. 19, in the state of the male screw 5 not being threadably mounted in the female thread portion 34, the bulging portion 33b has a reduced diameter toward the center side in the radial direction to an extent enabling passage through the hexagonal locking hole 14 of the base plate 11. In the state of the hexagonal engaging portion 33A being engaged in the hexagonal locking hole 14 of the base plate 11, when the male screw 5 is threadably mounted in the female thread portion 34, the hexagonal engaging portion 33A that is partitioned by the slits 33a (FIG. 20, FIG. 21) expands outward in the radial direction. At this time, a state results in which the trunk portion 33c contacts the inner surface of the hexagonal locking hole 14, and the bulging portion 33b locks with the lower surface 11b of the base plate 11. Thereby, upward movement of the structural body fixture 30A is restricted, and so the structural body fixture 30A and the base plate 11 can be reliably fixed. Here, when attaching the upper structural body 4 (refer to FIG. 1) to the structural body fixture 30A, after the hexagonal engaging portion 33A is engaged in the hexagonal locking hole 14, the fitting hole 42 of the upper structural body 4 (refer to FIG. 2) is meshed with the second fitting projection portion 31, and then the male screw 5 is threadably mounted in the female thread portion 34.

Note that in the structural body fixture 30A of the second embodiment, by removing the male screw 5, the trunk portion 33c and the bulging portion 33b return to the original reduced diameter state. For that reason, it is possible to extract the hexagonal engaging portion 33A upward from the hexagonal locking hole 14, and possible to remove it from the base plate 11.

Third Embodiment

Figure 22:
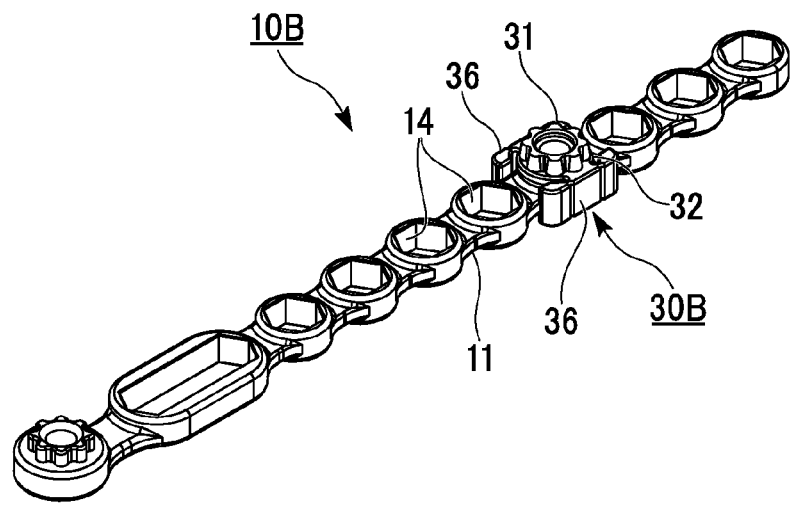
FIG. 22 is a perspective view that shows the entire constitution of the connection tool according to the third embodiment.
Figure 23:
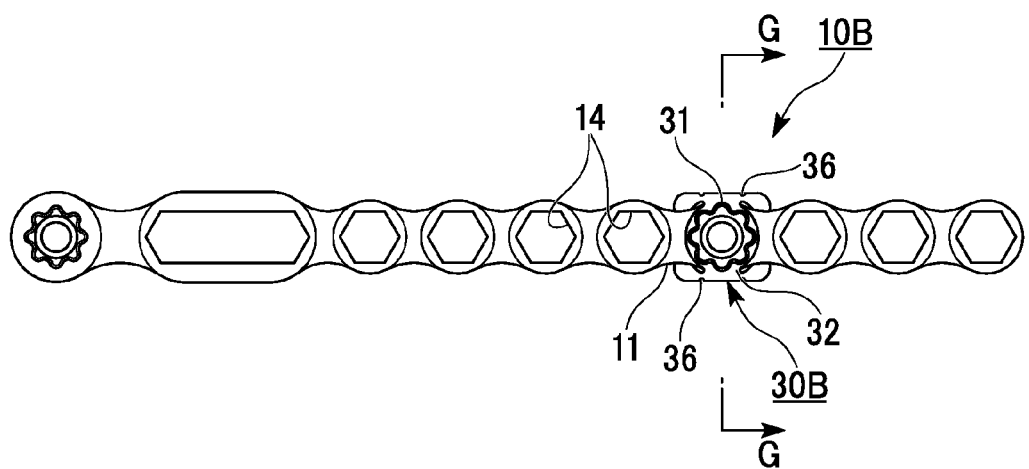
FIG. 23 is a top view of the connection tool shown in FIG. 22.
Figure 24:
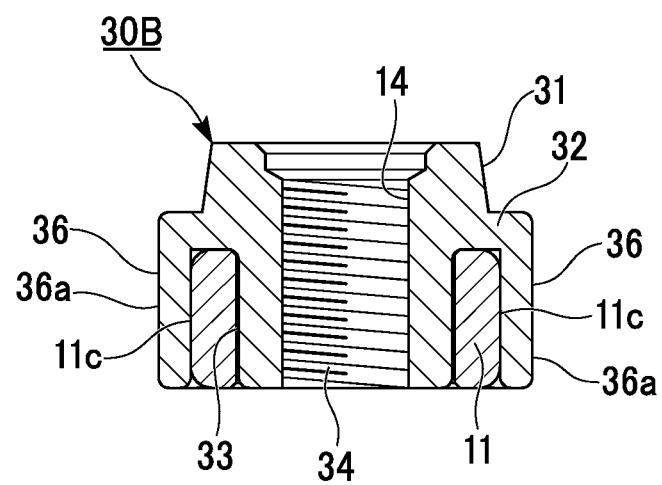
FIG. 24 is a cross-sectional view along the line G-G shown in FIG. 23.

Next, as shown in FIG. 22 to FIG. 24, the orthodontic connection tool 10B of the third embodiment caulks and holds the base plate 11 from the sides thereof (in the width direction of the base plate 11). That is to say, as shown in FIG. 22 to FIG. 29, in the structural body fixture 30B according to the third embodiment, the spring member 35 in the first embodiment described above is omitted, while the second fitting projection portion 31, the substrate portion 32, the hexagonal engaging portion 33, and the female thread portion 34 are provided. In the state of the hexagonal engaging portion 33 having been fit in the hexagonal locking hole 14, side walls 36 that extend downward so as to overlap both side surfaces 11c, 11c of the base plate 11 (refer to FIG. 24) are consecutively provided at the edges of the substrate portion 32.

Figure 25:
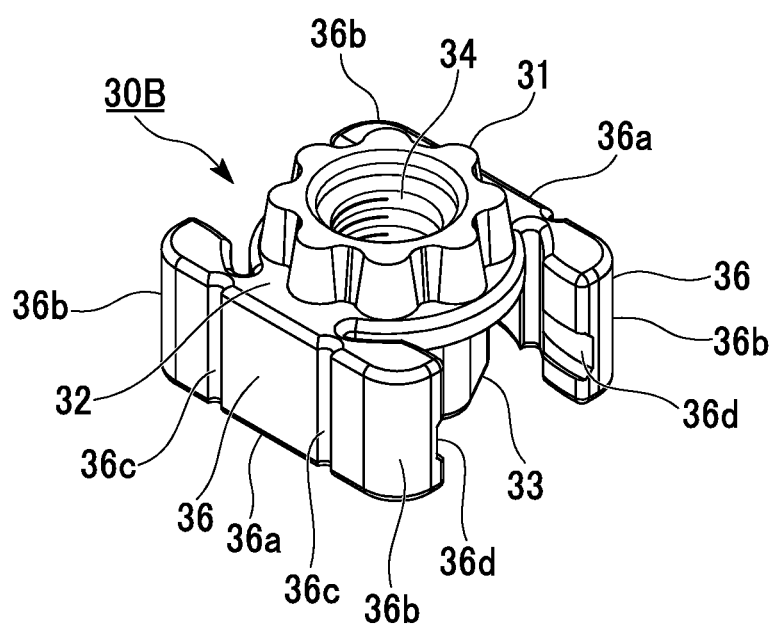
FIG. 25 is a perspective view that shows the entire constitution of the structural body fixture, seen from obliquely upward.
Figure 26:
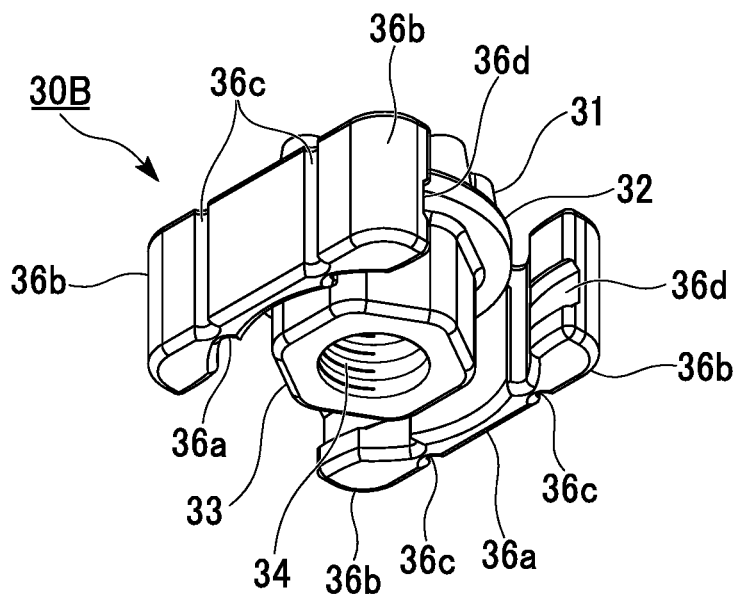
FIG. 26 is a perspective view that shows the entire constitution of the structural body fixture, seen from obliquely downward.
Figure 27:
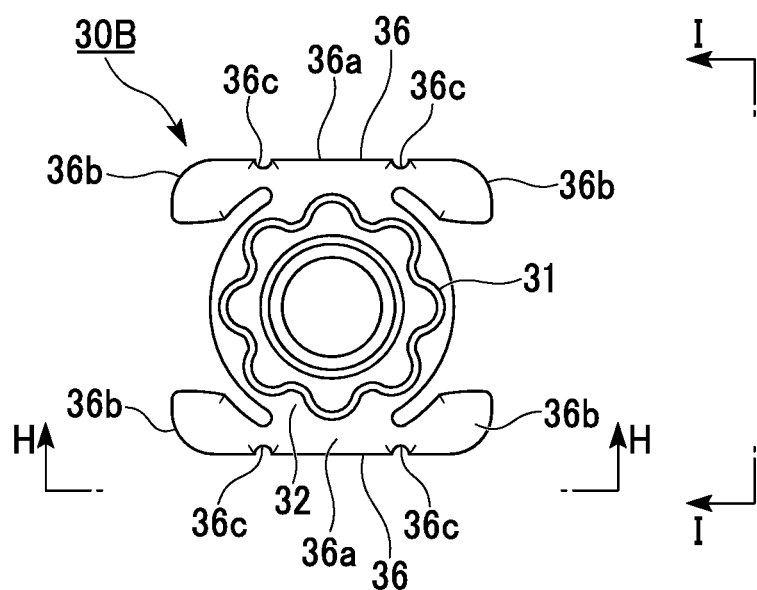
FIG. 27 is a top view of the structural body fixture.
Figure 28:
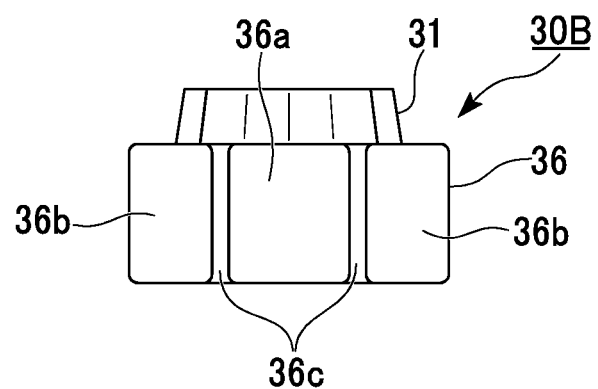
FIG. 28 is a side view of the structural body fixture, being an arrow view from the line H-H shown in FIG. 27.
Figure 29:
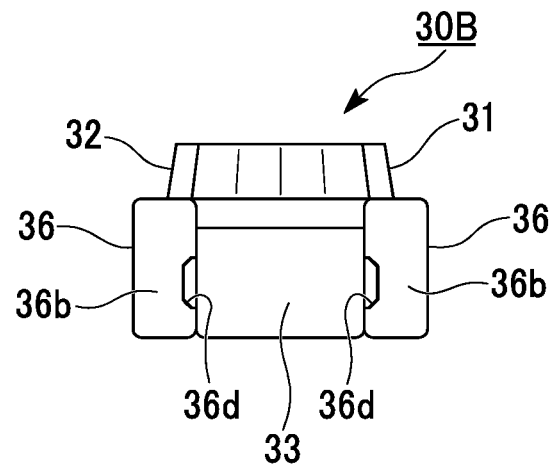
FIG. 29 is a side view of the structural body fixture, being an arrow view from the line I-I shown in FIG. 27.

In each side wall 36, a center portion 36a that is positioned in the center in the lateral direction is consecutively provided at the substrate portion 32, and caulking portions 36b, 36b (locking member) that jut out from the center portion 36a to both sides are provided. At the boundary between the center portion 36a and the caulking portion 36b, a pair of vertical grooves 36c, 36c extending over the entirety in the vertical direction are provided on the outer surface of the side wall 36, whereby the caulking portions 36b that sandwich the center portion 36a with the vertical grooves 36c serving as fulcrums are capable of flexing toward the inside (the base plate 11 side). Also, in the caulking portion 36b, as shown in FIG. 25, FIG. 26 and FIG. 29, a recessed portion 36d is provided at a position corresponding to the base plate 11, and this recessed portion 36d engages with the base plate 11 in the state of the caulking portion 36b being flexed.

In the structural body fixture 30B according to the third embodiment, in the state of the hexagonal engaging portion 33 being engaged in the hexagonal locking hole 14 of the base plate 11, each caulking portion 36b flexes to apply pressure to the base plate 11 side with the vertical groove 36c serving as a fulcrum. Thereby, the recessed portion 36d of the caulking portion 36b engages with the base plate 11, and upward movement of the structural body fixture 30B is restricted, and it is possible to reliably fix the structural body fixture 30B and the base plate 11.

Here, when attaching the upper structural body 4 (refer to FIG. 1) to the structural body fixture 30B, after engaging the hexagonal engaging portion 33 in the hexagonal locking hole 14, the fitting hole 42 of the upper structural body 4 is made to mesh with the second fitting projection portion 31 (refer to FIG. 2), after which the male screw 5 is threadably mounted in the female thread portion 34.

Fourth Embodiment

Figure 30:
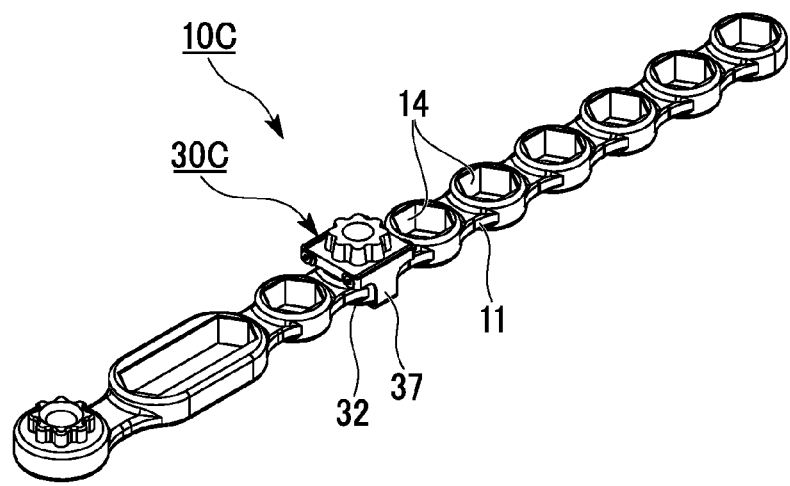
FIG. 30 is a perspective view that shows the entire constitution of the connection tool according to the fourth embodiment.
Figure 31:
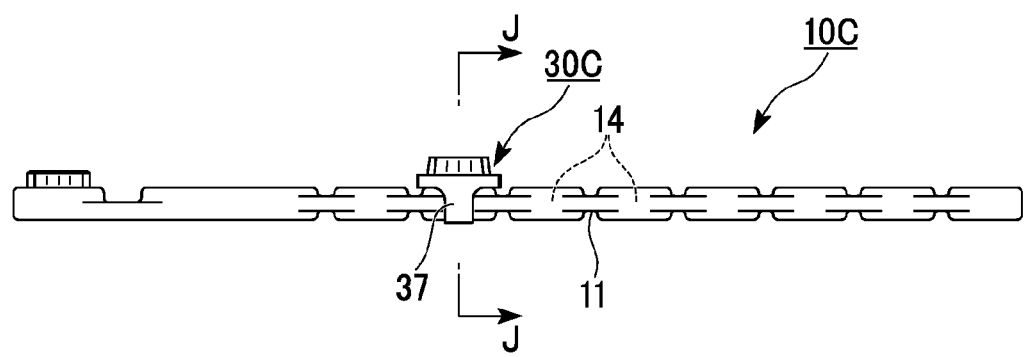
FIG. 31 is a side view of the connection tool shown in FIG. 30.
Figure 32:
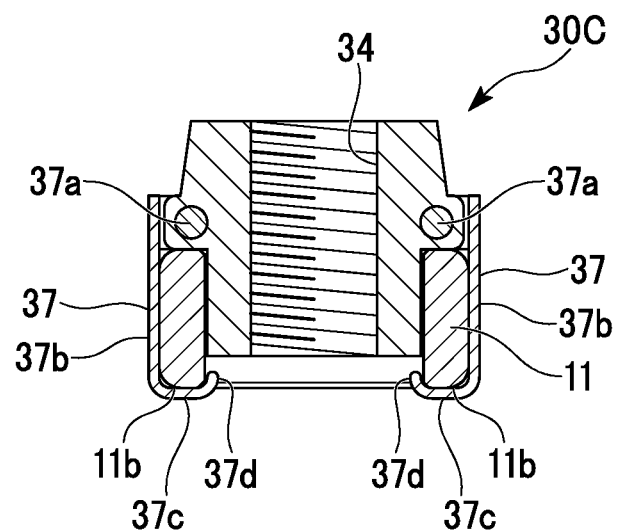
FIG. 32 is a cross-sectional view along the line J-J shown in FIG. 31.
Figure 33:
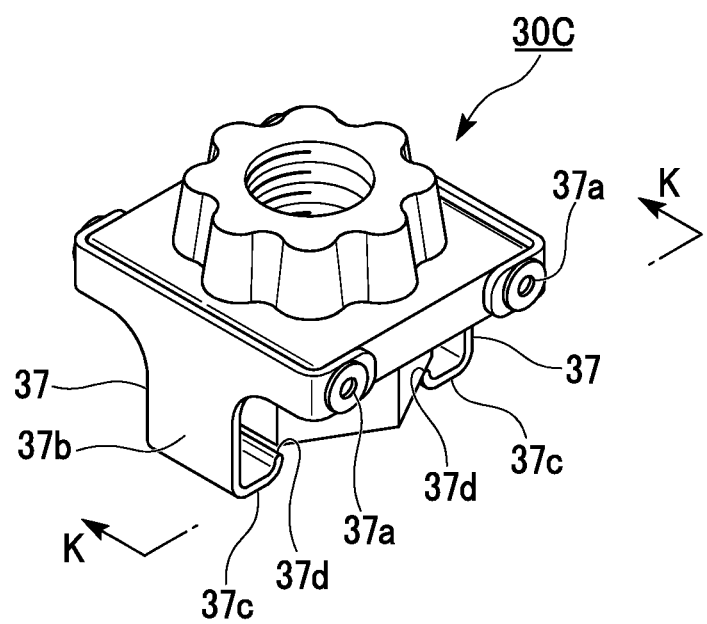
FIG. 33 is a perspective view that shows the entire constitution of the structural body fixture.

In the orthodontic connection tool 10C of the fourth embodiment shown in FIG. 30 to FIG. 32, a blade member 37 (locking member) is provided in place of the side wall 36 of the third embodiment described above (refer to FIG. 22 etc.)

That is to say, as shown from FIG. 30 to FIG. 34A and FIG. 34B, in the structural body fixture 30C of the fourth embodiment, planar-shaped blade members 37 are made to freely rotate centered on a rotation shaft 37a at both edges of the substrate portion 32 oppositely arranged in the width direction of the base plate 11. The rotation axis direction of the blade member 37 is the direction along the lengthwise direction of the base plate 11, in the state of the structural body fixture 30C being engaged in the hexagonal locking hole 14.

The blade member 37 is integrally provided with a blade main body 37b that has the rotation shaft 37a at one end, and a locking piece 37c that is consecutively provided at the other end (distal end) of the blade main body 37b and that can be fixed to the lower end of the base plate 11. When the blade main body 37b is oriented in the vertical direction, the locking piece 37c extends toward the inside (the base plate 11 side), and moreover a claw portion 37d is formed at the distal end thereof. In the state of the blade member 37 being locked on the base plate 11, the locking piece 37c is put in a position in contact with the lower surface 11b of the base plate 11, and at this time the claw portion 37d becomes caught in a state of having entered the hexagonal locking hole 14.

Figure 34A:
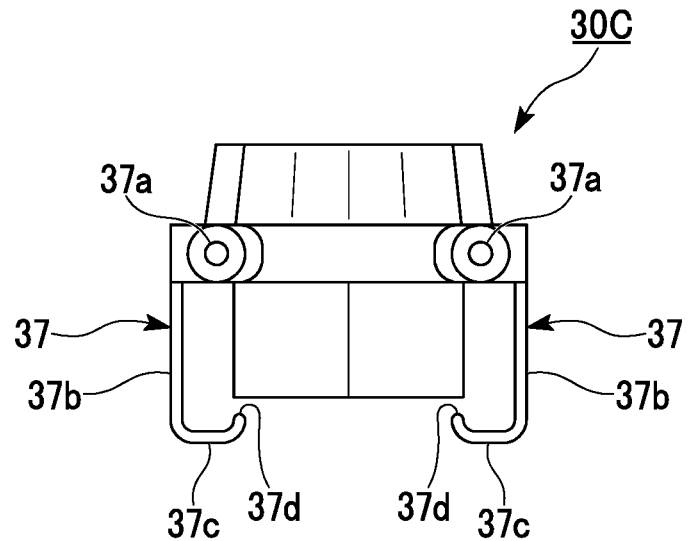
FIG. 34A is a drawing that shows the closed state of the blade members, being an arrow view from the line K-K shown in FIG. 33.
Figure 34B:
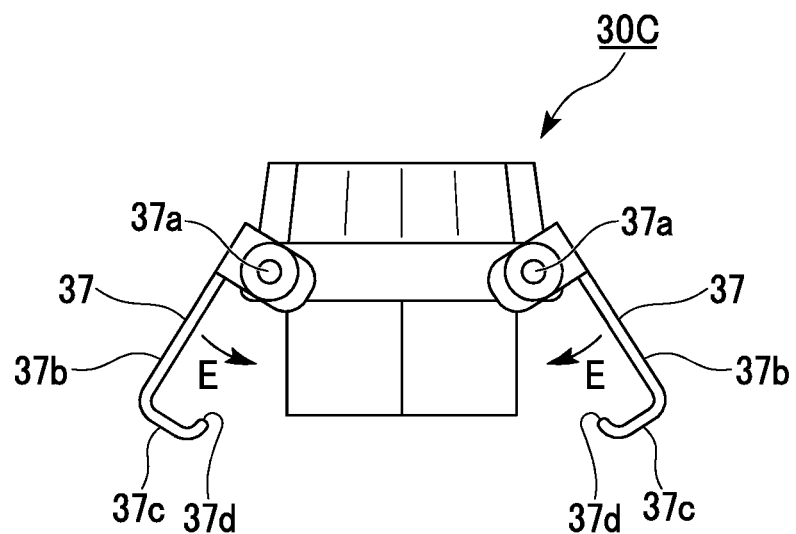
FIG. 34B is a drawing that shows the opened state of the blade members, being an arrow view from the line K-K shown in FIG. 33.

Here, as shown in FIG. 34A, in the blade member 37, the position at which the surface direction of the blade main body 37b is in a vertical direction is the locked state with respect to the base plate 11, and the position in which the surface direction of the blade main body 37b as shown in FIG. 34B is slanted is the opened state that releases the locked state.

In the structural body fixture 30C according to the fourth embodiment, the hexagonal engaging portion 33 is made to engage with the hexagonal locking hole 14 of the base plate 11 in the state of the blade members 37 being opened, and by rotating the blade members 37 in the directions of the arrows E of FIG. 34B, the locking pieces 37c engage with the base plate 11. That is to say, the claw portion 37d at the distal end of the locking piece 37c catches on the hexagonal locking hole 14 at the lower end of the base plate 11, upward movement of the structural body fixture 30C is restricted, and so it is possible to reliably fix the structural body fixture 30C and the base plate 11.

Note that, in this case, by grinding down and cutting away the coupling portion of the blade main body 37b and the substrate portion 32, it is possible to remove the structural body fixture 30C from the base plate 11 (hexagonal locking hole 14). Also, without being limited to such a removal method, the structural body fixture 30C may also be removed by releasing the engagement of the claw portions 37d with the base plate 11 by spreading out the blade members 37.

Fifth Embodiment

Figure 35:
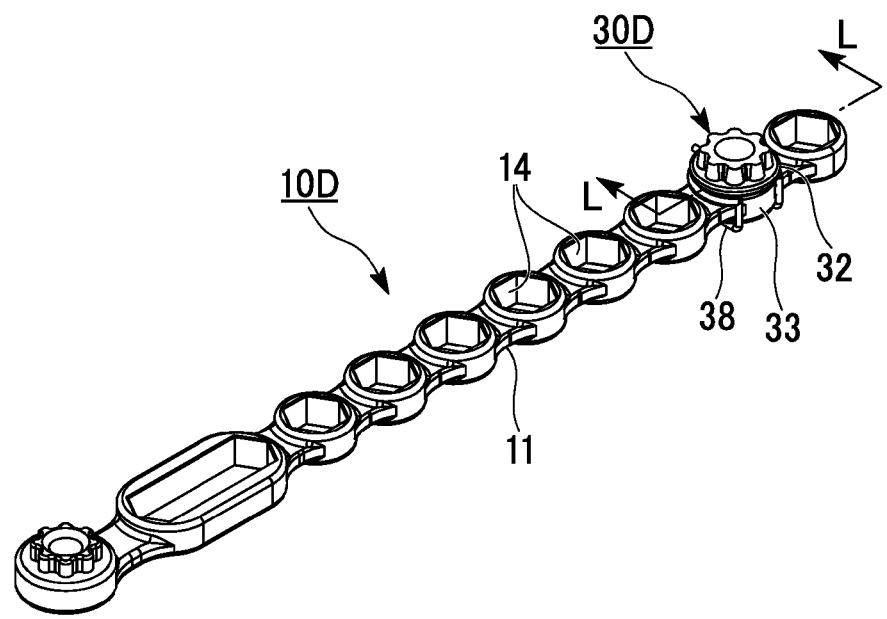
FIG. 35 is a perspective view that shows the entire constitution of the connection tool according to the fifth embodiment.
Figure 36:
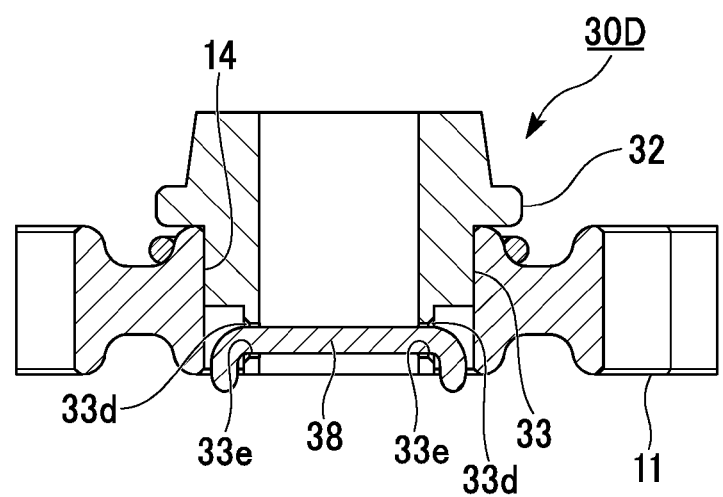
FIG. 36 is a cross-sectional view along the line L-L shown in FIG. 35.
Figure 37:
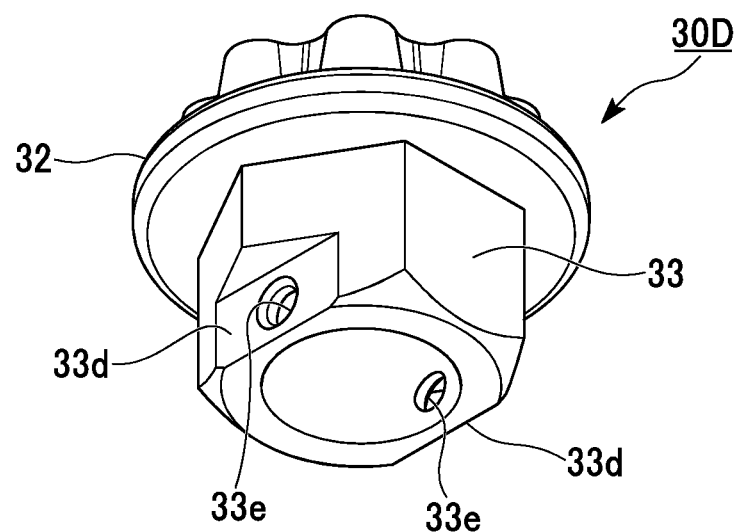
FIG. 37 is a perspective view that shows the entire constitution of the structural body fixture, being a drawing that omits the wire.

As shown in FIG. 35 to FIG. 37, the orthodontic connection tool 10D in the fifth embodiment is one that is fixed to the base plate 11 by a locking member due to the winding of a wire 38, instead of the aforementioned side walls 36 of the third embodiment (refer to FIG. 22 and the like) and the blade members 37 of the fourth embodiment. That is to say, in the structural body fixture 30D according to the fifth embodiment, a cutaway surface 33d that is perpendicular to the lengthwise direction of the base plate 11 is provided at the lower end of the hexagonal engaging portion 33, and a through-hole 33e for inserting the wire 38 is formed in this cutaway surface 33d. That is to say, the orientation of the wire 38 positioned within the hexagonal locking hole 14 that has been inserted in the pair of opposing through-holes 33e agrees with the lengthwise direction of the base plate 11. Note that in the state of the hexagonal engaging portion 33 being engaged in the hexagonal locking hole 14, the interval between the cutaway surface 33d and the hexagonal locking hole 14 is at least the dimension in which the wire 38 is arranged, that is to say, a dimension that is greater than the outer diameter of the wire 38.

In the structural body fixture 30D according to the fifth embodiment, in the state of the wire 38 being inserted in the pair of through-holes 33e, 33e in advance, the hexagonal engaging portion 33 is engaged in the hexagonal locking hole 14 of the base plate 11. Then, both ends of the wire 38 are extended from bottom to top along the side surface of the base plate 11, and moreover the wire 38 is wound around the peripheral edge of the hexagonal locking hole 14 at the lower side of the substrate portion 32 of the structure attachment portion 30D. Thereby, a state comes about in which the structural body fixture 30D is bound by the wire 38 to the base plate 11 (hexagonal locking hole 14), and so the structural body fixture 30D comes to be reliably fixed to the base plate 11.

Hereinabove, the orthodontic connection tool according to the present invention was described, but the present embodiment is not limited to the aforementioned embodiments, and suitable modifications are possible within a range that does not depart from the spirit of the present invention. For example, in the embodiments, the hexagonal head portion 23 of the screw 2 and the hexagonal engaging portion 33 of the structural body fixture 30 are engaged with the hexagonal locking holes 14 of the base plate 11, but they are not limited to this kind of structure. For example, with no hexagonal locking holes 14 or the locking oblong hole 13 provided in the base plate 11, the hexagonal head portion 23 need not be provided on the screw 2, and the hexagonal engaging portion 33 need not be provided on the structural body fixture 30. That is to say, another fixing means may be adopted, provided the base plate can be fixed to a bone by causing screws to directly pierce the base plate at arbitrary positions thereof, and a structural body fixture can be fixed to an arbitrary position of that base plate. Also, there is no need to limit the shape of the engaging portions of the screw 2 and the structural body fixture 30 with respect to the base plate 11 to a hexagonal shape, provided they have an angular shape of a regular polygon.

Also, the length of the oblong hole of the locking oblong hole 13 and the number of the hexagonal locking holes 14 in the base plate 11 are not restricted to the embodiments, and may be arbitrarily set. Moreover, the shape, size and the like of the upper structural body 4 can be modified.

Moreover, as the locking member that is provided in the structural body fixture 30, and 30A to 30D, the spring member 35 (first embodiment), the bulging portion 33b (second embodiment), the caulking portion 36b (third embodiment), the blade member 37 (fourth embodiment), and the wire 38 (fifth embodiment) were adopted, but there is no need to limit it to these forms. That is to say, the locking member need at least prevent the angular engaging portion of the structural body fixture from moving in the direction of slipping out from the angular locking hole of the base plate.

Also, the present embodiments adopted the elongated base plate 11 that extends in one direction, but it is not limited to this kind of shape. For example, it is possible to use a base plate with any shape appropriate to the conditions of use, such as a cross shape, a Y shape, or T shape in plan view.

In addition, it is possible to substitute the constituent elements in the aforedescribed embodiments with widely known constituent elements where appropriate within a scope that does not depart from the spirit of the present invention.

INDUSTRIAL APPLICABILITY

The orthodontic connection tool of the present invention is a simple structure that just causes the angular head portion of a screw and the angular engaging portion of a structural body fixture to be engaged in suitable positions selected among a plurality of angular locking holes, and so it is possible to easily attach and detach an upper structural body. Also, modification of the mounting position and number of the structural body fixture with respect to the base plate can also be easily performed without changing the position of the screw. Moreover, since it is a simple structure in which a plurality of the angular locking holes that are in common with the angular head portion of the screw and the angular engaging portion of the structural body fixture are provided in the base plate, it is possible to reduce manufacturing costs.

DESCRIPTION OF REFERENCE NUMERALS 1 implant structure
2, 2A, 2B screw
4 upper structural body
5 male screw
10, 10A, 10B, 10C, 10D connection tool
11 base plate
11b lower surface
12 first fitting projection portion
13 locking oblong hole
14 hexagonal locking hole (angular locking hole)
23 hexagonal head portion (angular head portion)
30, 30A, 30B, 30C, 30D structural body fixture
31 second fitting projection portion (fitting convex portion)
32 substrate portion
33, 33A hexagonal engaging portion (angular engaging portion)
33a slit
33b bulging portion (locking member)
33d cutaway surface
33e through-hole
34 female thread portion
35 spring member (locking member, holding member)
35c claw portion
36 side wall (holding member)
36b caulking portion (locking member)
36c vertical groove
36d recessed portion
37 blade member (locking member, holding member)
37c locking piece
37d claw portion
38 wire (locking member)
41 main body plate
42 fitting hole

The invention claimed is:

1. An orthodontic connection tool configured to attach to a screw that has been embedded in a bone in an oral cavity an upper structural body to which an orthodontic tool is fixed, the orthodontic connection tool comprising:
   a base plate that has a plurality of locking holes arranged at an equal interval in a lengthwise direction of the base plate and that is configured to engage with the screw; and
   a structural body fixture that has an engaging portion engaged with an arbitrary locking hole of the plurality of locking holes of the base plate thereof and that is configured to fix the upper structural body in a detachable manner,
   wherein the screw has an angular head portion in which a cross-sectional shape perpendicular to a screw axial direction is a polygonal shape;
   the plurality of locking holes of the base plate are angular locking holes arrayed in a plurality that engage the angular head portion of the screw; and
   the engaging portion of the structural body fixture is an angular engaging portion that engages the angular locking hole from an upper surface side of the base plate,
   wherein the structural body fixture has a locking member that restricts movement of the angular engaging portion in a direction of slipping out with respect to the angular locking hole, and
   wherein the structural body fixture is cylindrical and has a female thread portion that is formed in an inner periphery;
   the locking member has slits that extend upward in a vertical direction from a lower end of the angular engaging portion, and a male screw that is threadably mounted in the female thread portion; and
   in a state of the male screw being threadably mounted in the female thread portion, the angular engaging portion expands in diameter.

2. The orthodontic connection tool according to claim 1, wherein
   the upper structural body has a fitting hole that has a concavo-convex portion along an inner periphery; and
   the structural body fixture has a fitting convex portion that has a concavo-convex portion on an outer periphery that fits the fitting hole.

3. The orthodontic connection tool according to claim 1, wherein the base plate is elongated;
   an angular locking hole that is positioned at one end side in the lengthwise direction among the angular locking holes is a locking oblong hole that is long in the lengthwise direction.

* * * * *